(12) United States Patent
Leyrer et al.

(10) Patent No.: US 9,102,900 B2
(45) Date of Patent: Aug. 11, 2015

(54) INVERSE DISPERSION COMPRISING A CATIONIC POLYMER AND A STABILIZING AGENT

(71) Applicant: BASF SE, Ludwigshafen (DE)

(72) Inventors: Reinhold J. Leyrer, Dannstadt-Schauernheim (DE); Ouidad Benlahmar, Mannheim (DE); Volodymyr Boyko, Mannheim (DE); Jules Mikhael, Mannheim (DE); Frank Huelskoetter, Bad Dürkheim (DE); Mark Robert Sivik, Mason, OH (US); Travis Kyle Hodgdon, Cincinnati, OH (US); Jichun Shi, Loveland, OH (US)

(73) Assignee: BASF SE, Ludwigshafen (DE)

( * ) Notice: Subject to any disclaimer, the term of this patent is extended or adjusted under 35 U.S.C. 154(b) by 28 days.

(21) Appl. No.: 13/897,821

(22) Filed: May 20, 2013

(65) Prior Publication Data

US 2013/0310300 A1  Nov. 21, 2013

Related U.S. Application Data

(60) Provisional application No. 61/649,433, filed on May 21, 2012.

(51) Int. Cl.
| | | |
|---|---|---|
| *C11D 3/18* | (2006.01) | |
| *C11D 13/10* | (2006.01) | |
| *C11D 3/00* | (2006.01) | |
| *C11D 3/20* | (2006.01) | |
| *C11D 3/37* | (2006.01) | |
| *A61Q 5/12* | (2006.01) | |
| *A61K 8/81* | (2006.01) | |
| *A61K 8/90* | (2006.01) | |
| *A61K 8/06* | (2006.01) | |
| *A61Q 5/02* | (2006.01) | |
| *A61Q 5/06* | (2006.01) | |
| *A61Q 19/10* | (2006.01) | |

(52) U.S. Cl.
CPC .............. *C11D 3/001* (2013.01); *A61K 8/064* (2013.01); *A61K 8/8158* (2013.01); *A61K 8/90* (2013.01); *A61Q 5/12* (2013.01); *C11D 3/0015* (2013.01); *C11D 3/18* (2013.01); *C11D 3/2093* (2013.01); *C11D 3/3773* (2013.01); *A61Q 5/02* (2013.01); *A61Q 5/06* (2013.01); *A61Q 19/10* (2013.01)

(58) Field of Classification Search
CPC ......... C11D 3/18; C11D 3/3769; C11D 13/10

USPC ......... 510/330, 331, 342, 360, 417, 421, 437, 510/475, 504
See application file for complete search history.

(56) References Cited

U.S. PATENT DOCUMENTS

| | | | | |
|---|---|---|---|---|
| 4,528,321 | A | * | 7/1985 | Allen et al. .................. 524/761 |
| 2004/0071716 | A1 | | 4/2004 | Jansen et al. |
| 2005/0239957 | A1 | | 10/2005 | Pillsbury et al. |
| 2008/0275138 | A1 | | 11/2008 | Ridley et al. |
| 2008/0312343 | A1 | | 12/2008 | Braun et al. |
| 2011/0230387 | A1 | | 9/2011 | Leyrer et al. |
| 2013/0121944 | A1 | * | 5/2013 | Leyrer et al. ............... 424/70.16 |

FOREIGN PATENT DOCUMENTS

| | | | |
|---|---|---|---|
| EP | 172025 | A2 | 2/1986 |
| EP | 172723 | A2 | 2/1986 |
| EP | 172724 | A2 | 2/1986 |
| EP | 343840 | A2 | 11/1989 |
| EP | 1756168 | A2 | 2/2007 |
| GB | 2002400 | A | 2/1979 |
| WO | WO-9607689 | A1 | 3/1996 |
| WO | WO-03/102043 | A1 | 12/2003 |
| WO | WO-2004052942 | A1 | 6/2004 |
| WO | WO-2005097834 | A2 | 10/2005 |
| WO | WO-2009/019225 | A2 | 2/2009 |
| WO | WO 2010/079100 | * | 7/2010 ............. C11D 3/37 |
| WO | WO-2010078959 | A1 | 7/2010 |
| WO | WO-2010079100 | A1 | 7/2010 |

OTHER PUBLICATIONS

Schuck, "Size-Distribution Analysis of Macromolecules by Sedimentation Velocity Ultracentrifugation and Lamm Equation Modeling", Biophysical Journal, 2000, vol. 78, pp. 1606-1619.
European Search Report, EP 12 16 8760, Sep. 21, 2012.

* cited by examiner

*Primary Examiner* — Brian P Mruk
(74) *Attorney, Agent, or Firm* — Drinker Biddle & Reath LLP

(57) ABSTRACT

An inverse dispersion comprising
  i) at least one cationic polymer obtainable by the polymerization of
    a) at least one cationic monomer and optionally at least one nonionic monomer (compound A),
    b) optionally at least one crosslinker (compound B),
    c) optionally at least one chain transfer agent (compound C),
  ii) at least one stabilizing agent, wherein the stabilizing agent has one or more hydrophobic chains with more than 30 carbon atoms,
  iii) at least one non-aqueous carrier.

21 Claims, No Drawings

INVERSE DISPERSION COMPRISING A CATIONIC POLYMER AND A STABILIZING AGENT

CROSS-REFERENCE TO RELATED APPLICATIONS

This application claims benefit (under 35 U.S.C. §119(e)) of U.S. Provisional Application 61/649,433, filed May 21, 2012, which is incorporated herein by reference in its entirety.

BACKGROUND OF THE INVENTION

The present invention relates to an inverse dispersion comprising at least one cationic polymer and at least one stabilizing agent, wherein the stabilizing agent has one or more hydrophobic chains with more than 50 carbon atoms. The polymer is obtainable by polymerizing at least one cationic monomer and optionally at least one nonionic monomer. Furthermore, the present invention relates to a process for manufacturing the inverse dispersion by inverse emulsion polymerization.

WO03/102043 describes an aqueous formulation comprising a cationic polymer having: a) a water soluble ethylenically unsaturated monomer or blend of monomers comprising at least one cationic monomer; b) at least one cross-linking agent in an amount of more than 50 ppm by the weight of component a); c) and at least one chain transfer agent. The aqueous formulations can be used as thickeners in home care formulations.

EP 1 756 168 discloses spherical microparticles of hydrophilic acrylic polymers, whether anionic or cationic in charge, which have a typical particle size in the range of 0.1-2 microns, with an average particle size in the range of 0.5-1 micron. The polymeric microparticles are preferably manufactured by methods in which water-soluble vinyl addition monomers are polymerized utilizing a water-in-oil polymerization route. On stirring of any of the above liquid dispersion polymers into an aqueous system, the activator surfactant converts the hydrophobic carrier into an oil-in-water emulsion. By the term "activator surfactant" is meant a surfactant that activates the conversion of the hydrophobic carrier into an oil-in-water emulsion. At the same time the hydrophilic polymer expands on exposure to water but does not dissolve, resulting in a smooth and rapid viscosity increase. Typically the polymer particles swell to give a microparticulate thickening system comprising polymer particles having a typical particle size in the range of 2.5-5 microns in diameter. Since the water molecules move into the small polymer particles by osmosis, the osmotic effect experienced by the polymer particle is a balance between water and any electrolyte present in the system. Hence high electrolyte levels reduce the swelling of the polymer particles.

WO 2009/019225 reads on an aqueous dispersion of an alkali-soluble copolymer, said dispersion being suitable as an associative thickener. The copolymer comprises polymerized units of a) at least one ethylenically unsaturated carboxylic acid, b) at least one nonionic ethylenically unsaturated surfactant monomer, c) at least one $C_1$-$C_2$-alkyl methacrylate and d) at least one $C_2$-$C_4$-alkyl acrylate, where the alkyl chain length averaged over the number of alkyl groups of the alkyl acrylate is 2.1 to 4.0. The associative thickeners can be prepared by emulsion polymerization and are suitable for use in washing and cleaning compositions.

WO 2010/078959 relates to cationic polymer thickeners consisting of a crosslinked water-swellable cationic polymer comprising at least one cationic monomer and optionally nonionic or anionic monomers, said polymer comprising less than 25% of water-soluble polymer chains, based on the total weight of the polymer. The polymer also comprises a crosslinker in a concentration of 500 to 5000 ppm relative to the polymer. The cationic polymer is prepared by inverse emulsion polymerization.

WO 2010/079100 discloses fabric softener compositions comprising polymers according to WO 2010/078959.

US 2008/0312343 reads on inverse latex compositions and to the use thereof as a thickener and/or emulsifier, for example for production of cosmetic or pharmaceutical formulations. The inverse latex compositions comprise at least 50 to 80% by weight of at least one linear, branched or crosslinked organic polymer (P), at least 5 to 10% by weight of a water-in-oil-type emulsifier system, 5 to 45% by weight of at least one oil and up to 5% water. The polymer P comprises uncharged monomers and optionally cationic or anionic monomers. The inverse latex composition may optionally comprise up to 5% by weight of an oil-in-water-type emulsifier system. The inverse latex compositions can be prepared by inverse emulsion polymerization.

EP-A 172 025 relates to a dispersion in a continuous liquid phase of a polymer, which is formed by polymerization of an ethylenically unsaturated monomer comprising a hydrophobic group of at least eight carbon atoms and an ethylenically unsaturated monomer copolymerizable therewith. The dispersion is stable and essentially anhydrous, and comprises at least 40% by weight of polymer. In the polymerization, the copolymerizable, ethylenically unsaturated monomers used may, for example, be anionic monomers. The polymerization can be performed as an inverse emulsion polymerization.

EP-A 172 724 relates to polymers which are prepared by copolymerization of a) an ethylenically unsaturated monomer comprising a hydrophobic group with at least eight carbon atoms and b) water-soluble ethylenically unsaturated monomers. All monomers are soluble as a mixture in water, and the polymer is prepared by inverse emulsion polymerization. The polymer particles have a dry size of <4 μm. The monomer components b) used may be anionic monomers such as acrylic acid in the form of the free acid or as a water-soluble salt, and nonionic monomers such as acrylamide.

EP-A 172 723 describes a process for flocculating a suspension using a water-soluble, essentially linear polymer with a "single point intrinsic viscosity" of >3. The polymer is a copolymer of two or more ethylenically unsaturated monomers comprising at least 0.5% by weight of a monomer, comprising hydrophobic groups. The polymer may also be a cationic polymer.

BRIEF SUMMARY OF THE INVENTION

The problem underlying the present invention consists in the provision of novel thickeners and depositioning aids. The object is achieved by the inverse dispersion according to the invention comprising i) at least one cationic polymer obtainable by the polymerization of
   a) at least one cationic monomer and optionally at least one nonionic monomer (compound A),
   b) optionally at least one crosslinker (compound B),
   c) optionally at least one chain transfer agent (compound C), ii) at least one stabilizing agent, wherein the stabilizing agent has one or more hydrophobic chains with more than 30 carbon atoms, preferably more than 50 carbon atoms, iii) at least one non-aqueous carrier.

Preferably the ratio of the stabilizing agent to cationic polymer lies in the range of from 0.1 wt % to 20 wt % even more preferably in the range of from 1 wt % to 5 wt %.

A DETAILED DESCRIPTION OF THE INVENTION

The inverse dispersions according to the invention are characterized in that they have advantageous properties with regard to low coagulum content, high storage stability, deposition, shear dilution, stabilization and/or viscosity (thickening). Low coagulum is understood in the way that during the inverse emulsion polymerisation process no aggregation between the polymerising dispersed particles is visible. After the polymerisation process the same stabilising agent in addition avoids coalescence of the polymer particles, which may be induced by thermal motion, Brownian molecular movement or applied shear stress. Therefore the inverse dispersion has a high storage stability even at elevated temperatures and can easily be pumped at higher speed without inducing any visible coagulum or even any sedimentation of the polymer particles in the continuous oil phase. Moreover, they have the advantage that any redispersion required is achieved very quickly. Deposition is understood as meaning the deposition of the active ingredients of, for example, a fabric softener on a fiber during a washing operation. Applied to the present invention, this means that, for example, an inverse dispersion according to the invention comprising at least one cationic polymer (active ingredient) is present in a fabric softener and the fabric softener is used during or after the washing operation. The inverse dispersions according to the invention promote this deposition of the active ingredient during or after the washing operation to a considerable extent.

When assessing the shear dilution, it is important that the inverse dispersion, after being added to the aqueous formulation like fabric softener, where the phase inversion from a water in oil to an oil in water swollen polymer particle or dissolved polymer molecule is taking place, in its basic state is viscous and thick whereas it is thin upon stirring. The improved shear dilution has a positive effect on the life and properties of pumps during the production of the aqueous fabric softener, promotes convenient dosage for the consumer and promotes the residue-free use of the fabric softener, especially in the washing machines which have an automatic dosing device. The inverse dispersions according to the invention improve the stability of the thickener per se and that of the corresponding formulation. Also in the aqueous formulation containing the inventive polymer after phase inversion the settling or creaming of additionally added particles like vesicles, different soap phases, microcapsules, aluminium flakes or other particles is effectively prevented, irrespective of whether they are within the order of magnitude of nanometers, micrometers or millimeters. Moreover, they have the advantage that any redispersion required and the thickening are achieved very quickly.

Embodiments of the present invention in which the cationic polymers present in the inverse dispersion are prepared using little or no crosslinker are likewise associated with advantages. Due to the relatively high (water-)soluble components of the polymer, resoiling during a washing operation is reduced. Consequently, the article to be washed, even after repeated washing operations, has clean fibers which have been free effectively of soil particles, such that no graying is detected. Only very slight, if any, adhesion or redistribution of soil particles/polymers on the washed articles is observed, which can then be removed in the next washing cycle avoiding an accumulation effect. Also in that phase of the process the inventive stabilising agent is apparently supporting the stabilisation of the dispersed solid particles, especially with longer hydrophilic B blocks.

A further advantage of the inventive inverse dispersions, in which the cationic polymer is obtained by inverse emulsion polymerization, is manifested in surfactant-containing formulations because a high thickening performance and/or marked shear dilution are achieved in these formulations even at low thickener concentrations (<1% by weight).

The inventive inverse dispersion comprises, as component i), at least one cationic polymer which is obtainable by the polymerization of compound A and optionally B and C, as compound ii) a stabilizing agent and as compound iii) a non-aqueous carrier.

Compound i): Cationic Polymer

The cationic monomer according to compound A is preferably selected from a compound of the formula (I)

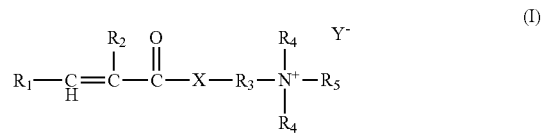

where
$R_1$ is H or $C_1$-$C_4$-alkyl,
$R_2$ is H or methyl,
$R_3$ is C, $C_1$-$C_4$-alkylene,
$R_4$, $R_5$ and $R_6$ are each independently H or $C_1$-$C_{30}$-alkyl,
X is —O— or —NH— and
Y is Cl; Br; I; hydrogensulfate or methosulfate.

In one embodiment of the present invention, it is preferred that, in the cationic monomer of the formula (I),
i) $R_1$ and $R_2$ are each H or
ii) $R_1$ is H and $R_2$ is $CH_3$ or preferably also H.

Particularly preferred cationic monomers are [2-(Acryloyloxy)ethyl]trimethylammonium chloride also referred to as dimethylaminoethyl acrylate methochloride (DMA3*MeCl) or trimethyl-[2-(2-methylprop-2-enoyloxy)ethyl]azanium chloride also referred as dimethylaminoethyl methacrylate methochloride (DMAEMA*MeCl).

Compound A may comprise at least one nonionic monomer. Apart from the nitrogen-containing monomers described below, such as, for example, the compounds according to formula (II), esters of anionic monomers are suitable as nonionic monomers. Such nonionic monomers are preferably the methyl or ethyl esters of acrylic acid, methacrylic acid, itaconic acid or maleic acid such as ethyl acrylate or methyl acrylate. Additionally preferred are the corresponding dimethylamino-substituted esters such as dimethylaminoethyl (meth)acrylate.

Preferably, the nonionic monomer according to compound A in the cationic polymer is selected from N-vinylpyrrolidone, N-vinylimidazole or a compound according to the formula (II)

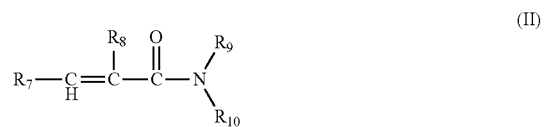

where
R$_7$ is H or C$_1$-C$_4$-alkyl,
R$_8$ is H or methyl, and
R$_9$ and R$_{10}$, independently of one another, are H or C$_1$-C$_{30}$-alkyl.

The nonionic monomer is particularly preferably acrylamide, methacrylamide or dialkylamino-acrylamide.

The nonionic monomer may also be an ethylenically unsaturated associative monomer selected from a compound of the following formula

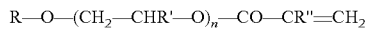

where
R is C$_6$-C$_{50}$-alkyl, preferably C$_8$-C$_{30}$-alkyl, especially C$_{16}$-C$_{22}$-alkyl,
R' is H or C$_1$-C$_4$-alkyl, preferably H,
R" is H or methyl,
n is an integer from 0 to 100, preferably 3 to 50, especially 25.

These compounds can be methacrylates of fatty alcohol ethoxylates.

The R radical in the compounds may also be present as a mixture of radicals with different chain lengths, such as C$_{16}$ and C$_{18}$. One example thereof is C$_{16}$-C$_{18}$-fatty alcohol-(ethylene glycol)$_{25}$-ether methacrylate, where both C$_{16}$ and C$_{18}$ fatty alcohol radicals (in non-negligible amounts) are present as a mixture. In contrast, for example behenyl-25 methacrylate and cetyl-25 methacrylate, the particular R radical is not present as a mixture but as a C$_{22}$ or C$_{16}$ chain. Other chain lengths occur only in the form of impurities. The number "25" in these compounds represents the size of the variables n.

The aqueous phase during the inverse emulsion polymerization may thus comprise, for example, a chain transfer agent, a crosslinker, a cationic monomer and optionally an uncharged monomer, and/or also an associative monomer giving hydrophobic hydrophobic interaction for example via van der Waals forces, and optionally further components. Suitable further components are, for example, complexing agents for salts such as pentasodium diethylenetriaminepentaacetic acid, or compounds which can be used to adjust the pH, such as citric acid.

In a preferred embodiment of the present invention, compound i), i.e. the cationic polymer is obtainable by the polymerization of at least one cationic monomer. In another preferred embodiment of the present invention, compound i), i.e. the cationic polymer is obtainable by the polymerization of at least one cationic monomer and of at least one nonionic monomer. Preferably, the weight ratio of cationic monomer to nonionic monomer lies in the range of from 90/10 to 10/90, more preferably the weight ratio of cationic monomer to nonionic monomer lies in the range of from 75/25 to 40/60 and even mostly preferably in the range of from 60/40 to 50/50.

In the preparation of the polymer by polymerization, at least one crosslinker may optionally be present as compound B. Suitable crosslinkers are known to the person skilled in the art. Preferably, in the polymer, the crosslinker according to compound B is selected from divinylbenzene; tetraallylammonium chloride; allyl acrylates; allyl methacrylates; diacrylates and dimethacrylates of glycols or polyglycols; butadiene; 1,7-octadiene, allylacrylamides or allylmethacrylamides; bisacrylamidoacetic acid; N,N'-methylenebisacrylamide or polyol polyallyl ethers such as polyallyl sucrose or pentaerythritol triallyl ether. Also suitable as a preferred crosslinker is dialkyldimethylammonium chloride.

Furthermore, during the preparation of the polymer by polymerization, at least one chain transfer agent can be used as compound C. Suitable chain transfer agents are known to the person skilled in the art. Preferred chain transfer agents according to compound C are selected from mercaptan, lactic acid, formic acid, isopropanol or hypophosphites.

Preferably, the inventive inverse dispersion comprises at least one cationic polymer obtainable by the polymerization of
a) 20 to 99.99% by weight, preferably 95 to 99.95% by weight (based on the polymer), of at least one cationic monomer, and optionally at least one nonionic monomer,
b) 0 to 0.3% by weight, preferably from 0.0075 to 0.1%, even more preferably from 0.01 to 0.1% by weight (based on the polymer), even more preferably from 0.05 to 0.1% by weight of optionally at least one crosslinker,
c) 0 to 3% by weight, preferably 0.05 to 0.5% by weight (based on the polymer), of optionally at least one chain transfer agent, in the presence of one stabilizing agent, wherein the stabilizing agent has one or more hydrophobic chains with more than 50 carbon atoms and preferably the ratio of stabilizing agent to cationic polymer lies in the range of from 0.1 wt % to 10 wt %.

In a further embodiment of the present invention, from 10% to 100% by weight based on the total weight of the cationic polymer are water-soluble polymers, preferably 25% to 50% by weight based on the total weight of the cationic polymer. The water-soluble polymers of the cationic polymer have a sedimentation coefficient of from 0.1 to 100Sved, preferably of from 1 to 30Sved in aqueous media. The solubility of the cationic polymer is determined by methods known to those skilled in the art, by admixing the cationic polymer present in the inventive thickener with a defined amount of water (see, for example, EP-A 343 840 or preferably the determination method of the sedimentation coefficient in the unit of svedberg (sved) according to P. Schuck, 'Size-distribution analysis of macromolecules by sedimentation velocity ultracentrifugation and Lamm equation modeling', Biophysical Journal 78, (3) (2000), 1606-1619).

In a further preferred embodiment of the present invention, from 0% to 90% by weight based on the total weight of the cationic polymer are crosslinked water-swellable polymers, preferably from 50% to 75% by weight based on the total weight of the cationic polymer. The crosslinked water-swellable polymers have a sedimentation coefficient of more than 300Sved, preferably between 600 and 20 000Sved in aqueous media.

In an especially preferred embodiment of the present invention, the proportion of crosslinker (compound B) used in the polymerization of the cationic polymer is less than 1%, preferably less than 0.1% by weight (based on the total amount of compounds A to C).

More preferably, no crosslinker is used in the polymerization of the cationic polymer.

Compound ii): Stabilizing Agent

The inventive inverse dispersion further comprises, as compound ii), at least one stabilizing agent. Stabilizing agents as such are known in principle to those skilled in the art.

Suitable stabilizing agents are preferably surfactants or polymeric emulsifiers.

Surfactants are for example anionic, nonionic, cationic and/or amphoteric surfactants. Preference is given to using anionic and/or nonionic surfactants, which are disclosed, for example, in US2004/0071716 A1.

In the above mentioned state of the art there are described stabilizing agent with low HLB values to stabilise the disperse hydrophilic polymer particles in the hydrophobic continuous phase. These agents have a hydrophilic part like mono or oligo-glucoside or the carbon acid containing part of a copolymer and a hydrophobic part like for example alkyl chains with different lengths. The hydrophilic part is dissolved in the hydrophilic polymer particle and the hydrophobic part is concentrated on the surface of the particle and dissolved in the hydrophobic continuous phase forming a "hydrophobic hairy layer" around the hydrophilic cationic polymer particle. Thus the effect of sterical stabilisation prevents the destabilisation and the coagulation of the hydrophilic particles. The stabilising effect is as important both during the inverse emulsion polymerisation process avoiding larger particles (coagulum) and for the storage stability of the inverse dispersion, avoiding particle sedimentation before it is used in aqueous formulations. The sterical stabilisation is especially also effective in high electrolyte containing dispersions or formulations.

According to this invention it has now been found that if the stabilizing agent has one or more hydrophobic units with more than 30 carbon atoms per hydrophobic unit, preferably more than 50 carbon atoms per hydrophobic unit, this results in a dramatic increase of the stabilizing effect for the hydrophilic polymer particles dispersed in the hydrophobic continuous phase. Said carbon atoms may preferably be part of $CH_2$ or $CH(C_1-C_8\ alkyl)$ or $C(CH_3)_2$ groups. In general all emulsifiers or polymeric stabilizers containing more than 30 carbon atoms per hydrophobic unit, preferably more than 50 carbon atoms per hydrophobic unit and less than 300 carbon atoms per hydrophobic unit, preferably less than 150 carbon atoms per hydrophobic unit are claimed for the purpose of the present invention. Optionally in said hydrophobic chains less than every seventh, preferably less than every eleventh $CH_2$ groups can be replaced by other atoms like oxygen, nitrogen, sulphur, phosphorus or by groups like carbonate, isocyanate, carbamide, esters or others in an amount that they do not essentially disturb the hydrophobic character of the unit in order to get the low HLB-values as described below. Block-, graft- or comb-structure, are preferably based on polyhydroxystearic acid. In the block-structure the AB- or especially ABA-blocks are preferred. In the ABA block-structure the A block is preferably based on polyhydroxystearic acid and the B block on polyalkylene oxide, preferably on polyethylene oxide, even more preferably on polyethylene oxide comprising 15 ethylene oxide units or 30 ethylene oxide units or 75 ethylene oxide units Preferred stabilizing agents have a molecular weight of at least 3000 g/mol, preferably of least 5000 g/mol and of at most 16000 g/mol, preferably of at most 10000 g/mol.

It is additionally preferred in the context of the present invention to use a stabilizing surfactant which has a (relatively) low HLB (hydrophilic-lipophilic balance) value. The stabilizing agent preferably has an HLB value of 1 to 12, more preferably of 3 to 9 and especially preferably of 5 to 7.

The preferred concentration of these inventive stabilising surfactants lies between 0.1% and 10% preferably between 1% to 5% related to the polymer.

The polymeric emulsifiers are preferably a block copolymers having a general formula A-COO—B—OOC-A, in which B is the divalent residue of a water-soluble polyalkylene glycol and A is the residue of an oil-soluble complex monocarboxylic acid. Such polymeric emulsifiers, as well as the preparation thereof, have been disclosed in GB 2002400 and WO9607689, the contents of which are herewith incorporated by reference. The emulsifiers, as described in GB2002400, are emulsifiers wherein A has a molecular weight of at least 500 and is the residue of an oil-soluble complex monocarboxylic acid, i.e. a fatty acid. These complex monocarboxylic acids may be represented by the general formula:

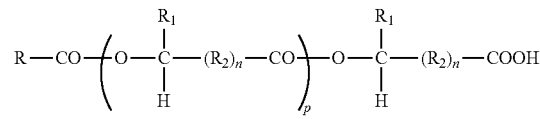

in which
R is hydrogen or a monovalent hydrocarbon or substituted hydrocarbon group;
R1 is hydrogen or a monovalent C1 to C24 hydro-carbon group;
R2 is a divalent C1 to C24 hydrocarbon group;
n is zero or 1;
p is an integer from zero to 200.

The units between the brackets in formula 1 may be all the same or they may differ in respect of R1, R2 and n. The quantity p will not normally have the same unique value for all molecules of the complex acid but will be statistically distributed about an average value lying within the range stated, as is commonplace in polymeric materials. Polymeric component B has a molecular weight of at least 500 and is the divalent residue of a water-soluble polyalkylene glycol having the general formula

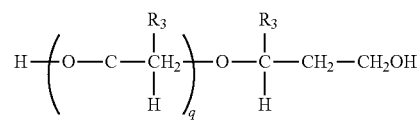

wherein
R3 is hydrogen or a C1 to C3 alkyl group;
q is an integer from 10 up to 500.

Most preferred emulsifiers used in the invention are e.g. PEG 30 Dipolyhydroxystearate. Another similar emulsifier for use with the invention are block copolymers (A-B-A) of polyethylene glycol and polyhydroxystearic acid with a mol weight of approximately 5000.

Furthermore the use of these ABA type block copolymers lead to water-in-oil emulsions having excellent stability during storage thus improving the shelf life of said emulsions. The resulting water-in-oil emulsions are stable and fluid at low temperatures, especially at 25° C.

Compound iii): Non-Aqueous Carrier

In the inventive thickener, the cationic polymer may be present dispersed in an oil phase, preferably as an inverse dispersion, water-in-oil dispersion, or as a dispersed anhydrous cationic polymer in oil, i.e. the non-aqueous carrier is an oil phase A suitable oil phase comprises one or more high boiling oils with boilings points above 220° C. are for example, 2-ethylhexyl stearate and hydroheated heavy naphtha, and suitable low-boiling oils with boilings points below 220° C., for example, dearomatized aliphatic hydrocarbons or mineral oils of low viscosity, as defined in WO 2005/097834.

The present invention further provides a process for the manufacture of an inverse dispersion comprising
 i) at least one cationic polymer obtainable by the polymerization of
  a) at least one cationic monomer and optionally at least one nonionic monomer (compound A), b) optionally at least one crosslinker (compound B),
c) optionally at least one chain transfer agent (compound C),
ii) at least one stabilizing agent, wherein the stabilizing agent has one or more hydrophobic chains with more than 30 carbon atoms, preferably more than 50 carbon atoms,
iii) at least one non-aqueous carrier,
wherein the inverse dispersion is obtained by inverse emulsion polymerization, optionally followed by distillation by means of the liquid dispersion polymer technology.

In the context of the present invention, the cationic polymer is prepared by inverse emulsion polymerization. Inverse emulsion polymerization is as such known to the person skilled in the art. Inverse emulsion polymerization is understood by the person skilled in the art generally to mean polymerization processes according to the following definition: the hydrophilic monomers are dispersed in a hydrophobic oil phase. The polymerization is effected directly in these hydrophilic monomer particles by addition of initiator.

In addition, it is preferred that, after the inverse emulsion polymerization, at least a portion of water and at least a portion of the low-boiling constituents of the oil phase are distilled off, especially by means of LDP technology (Liquid Dispersion Polymer Technology). LDP technology as such is known to those skilled in the art; it is described, for example, in WO 2005/097834. An inverse dispersion is thus obtained.

The information which follows, unless stated otherwise, applies to all kinds of emulsion polymerization, for example to emulsion polymerization in water, which then constitutes the continuous phase, and especially also to inverse emulsion polymerization in which the hydrophobic oil phase constitutes the continuous phase.

The aqueous phase comprises, for example, a chain transfer agent, a crosslinker, a cationic monomer and optionally an uncharged monomer, and optionally further components. Suitable further components are, for example, complexing agents for salts such as pentasodium diethyllenetriaminepentaacetic acid, or compounds which can be used to adjust the pH, such as citric acid.

The oil phase preferably comprises an emulsifier, a stabilizing agent, a high-boiling oil, and a low-boiling oil. In addition, the oil phase may optionally comprise a nonionic monomer or oil-soluble surfactants, activators inducing the phase change during dilution with water, cross-linkers, chain transfer agents or initiator components.

A suitable polymerization initiator is used for the polymerization. Redox initiators and/or thermally activatable free-radical polymerization initiators are preferred.

Suitable thermally activatable free-radical initiators or the oxidative component of the redox initiator pair are in particular those of the peroxy and azo type. These include hydrogen peroxide, peracetic acid, t-butyl hydroperoxide, di-t-butyl peroxide, dibenzoyl peroxide, benzoyl hydroperoxide, 2,4-dichlorobenzoyl peroxide, 2,5-dimethyl-2,5-bis(hydroperoxy)hexane, perbenzoic acid, t-butyl peroxypivalate, t-butyl peracetate, dilauroyl peroxide, dicapryloyl peroxide, distearoyl peroxide, dibenzoyl peroxide, diisopropyl peroxydicarbonate, didecyl peroxydicarbonate, dieicosyl peroxydicarbonate, di-t-butyl perbenzoate, azobisisobutyronitrile, 2,2'-azobis-2,4-dimethylvaleronitrile, ammonium persulfate, potassium persulfate, sodium persulfate and sodium perphosphate.

The persulfates (peroxodisulfates), especially sodium persulfate, are most preferred.

The inverse dispersion can contain a mixture of the oxidizing component of redox initiator like t-Butylhydroperoxide and potassium bromate and the preferred reducing component is sodium hydrogen sulfite.

In the performance of the emulsion polymerization, the initiator is used in a sufficient amount to initiate the polymerization reaction. The initiator is typically used in an amount of about 0.01 to 3% by weight, based on the total weight of the monomers used. The amount of initiator is preferably about 0.05 to 2% by weight and especially 0.1 to 1% by weight, based on the total weight of the monomers used.

The emulsion polymerization is effected typically at 0° C. to 100° C. It can be performed either as a batch process or in the form of a feed process. In the feed method, at least a portion of the polymerization initiator and optionally a portion of the monomers are initially charged and heated to polymerization temperature, and then the rest of the polymerization mixture is supplied, typically over several separate feeds, one or more of which comprise the monomers in pure or emulsified form, continuously or stepwise while maintaining the polymerization. Preference is given to supplying the monomer in the form of a monomer emulsion. In parallel to the monomer supply, further polymerization initiator can be metered in.

In preferred embodiments, the entire amount of initiator is initially charged, i.e. there is no further metering of initiator parallel to the monomer feed.

In a preferred embodiment, the thermally activatable free-radical polymerization initiator is therefore initially charged completely and the monomer mixture, preferably in the form of a monomer emulsion, is fed in. Before the feeding of the monomer mixture is started, the initial charge is brought to the activation temperature of the thermally activatable free-radical polymerization initiator or a higher temperature. The activation temperature is considered to be the temperature at which at least half of the initiator has decomposed after one hour.

In another preferred preparation method, the cationic polymer is obtained by polymerization of a monomer mixture in the presence of a redox initiator system. A redox initiator system comprises at least one oxidizing agent component and at least one reducing agent component, in which case heavy metal ions are preferably additionally present as a catalyst in the reaction medium, for example salts of cerium, manganese or iron(II).

Suitable oxidizing agent components are, for example, sodium or potassium bromate, peroxides and/or hydroperoxides such as hydrogen peroxide, tert-butyl hydroperoxide, cumene hydroperoxide, pinane hydroperoxide, diisopropylphenyl hydroperoxide, dicyclohexyl percarbonate, dibenzoyl peroxide, dilauroyl peroxide and diacetyl peroxide. Hydrogen peroxide and tert-butyl hydroperoxide are preferred.

Suitable reducing agent components are alkali metal sulfites, alkali metal dithionites, alkali metal hyposulfites, sodium hydrogensulfite, Rongalit C (sodium formaldehydesulfoxylate), mono- and dihydroxyacetone, sugars (e.g. glucose or dextrose), ascorbic acid and salts thereof, acetone bisulfite adduct and/or an alkali metal salt of hydroxymethanesulfinic acid. Sodium hydrogensulfite or sodium metabisulfite is preferred.

Suitable reducing agent components or catalysts are also iron(II) salts, for example iron(II) sulfate, tin(II) salts, for example tin(II) chloride, titanium(III) salts such as titanium (III) sulfate.

The amounts of oxidizing agent used are 0.001 to 5.0% by weight, preferably from 0.005 to 1.0% by weight and more preferably from 0.01 to 0.5% by weight, based on the total weight of the monomers used. Reducing agents are used in amounts of 0.001 to 2.0% by weight, preferably of 0.005 to 1.0% by weight and more preferably of 0.01 to 0.5% by weight, based on the total weight of the monomers used.

A particularly preferred redox initiator system is the sodium peroxodisulfate/sodium hydrogensulfite system, for example 0.001 to 5.0% by weight of sodium peroxodisulfate and 0.001 to 2.0% by weight of sodium hydrogensulfite, especially 0.005 to 1.0% by weight of sodium peroxodisulfate and 0.005 to 1.0% by weight of sodium hydrogensulfite, more preferably 0.01 to 0.5% by weight of sodium peroxodisulfate and 0.01 to 0.5% by weight of sodium hydrogensulfite.

A further particularly preferred redox initiator system is the t-butyl hydroperoxide/hydrogen peroxide/ascorbic acid system, for example 0.001 to 5.0% by weight of t-butyl hydroperoxide, 0.001 to 5.0% by weight of hydrogen peroxide and 0.001 to 2.0% by weight of ascorbic acid, especially 0.005 to 1.0% by weight of t-butyl hydroperoxide, 0.005 to 1.0% by weight of hydrogen peroxide and 0.005 to 1.0% by weight of ascorbic acid, more preferably 0.01 to 0.5% by weight of t-butyl hydroperoxide, 0.01 to 0.5% by weight of hydrogen peroxide and 0.01 to 0.5% by weight of ascorbic acid.

In a preferred embodiment of this invention, both thermal initiators and redox initiators can be used together and one or more components of the used initiator compounds can be pre-fed partially or completely.

Emulsifiers, stabilizers, low-boiling oils and high-boiling oils as such are known to those skilled in the art. These compounds can be used individually or in the form of mixtures.

Typical emulsifiers in addition to the stabilizing agent are anionic emulsifiers, for example sodium laurylsulfate, sodium tridecyl ether sulfates, dioctylsulfosuccinate sodium salt and sodium salts of alkylaryl polyether sulfonates; and nonionic emulsifiers, for example alkylaryl polyether alcohols and ethylene oxide-propylene oxide copolymers. Sorbitan trioleate is likewise suitable as an emulsifier.

Preferred emulsifiers have the following general formula:

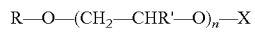

in which R is $C_6$-$C_{30}$-alkyl,
R' is hydrogen or methyl,
X is hydrogen or $SO_3M$,
M is hydrogen or one alkali metal, and
n is an integer from 2 to 100.

Suitable stabilizers are described, for example, in EP-A 172 025 or EP-A 172 724. Preferred stabilizers are copolymers of stearyl methacrylate and methacrylic acid.

Suitable high-boiling oils are, for example, 2-ethylhexyl stearate and hydroheated heavy naphtha, and suitable low-boiling oils are, for example, dearomatized aliphatic hydrocarbons or mineral oils of low viscosity.

In a preferred embodiment of the present invention, compound A is completely or partially added to the oil phase in the inverse emulsion polymerization In the inverse emulsion polymerization, the temperature can be kept constant or else it can rise. The rise in the temperature can be performed continuously or in stages. For example, the temperature can rise by 0.1 to 10° C. per minute during the polymerization, preferably from 0.5 to 3° C. per minute. The temperature rise is controlled by the rate of initiator addition. The starting temperature value may be 0 to 30° C., preferably 10 to 20° C.

In another embodiment of the present invention, the temperature in the inverse emulsion polymerization is kept constant (cold method); the temperature is 0 to 30° C., preferably 10 to 20° C. In a further embodiment of the present invention, the temperature is kept constant within a higher temperature range (hot method). The temperature in the polymerization is 40 to 150° C., preferably 70 to 120° C.

In a particularly preferred embodiment of the present invention, the temperature is kept constant during the inverse emulsion polymerization, the temperature being at least 40° C., preferably 50 to 90° C.

If, in the context of the present invention, the temperature is kept constant in a polymerization, especially in an inverse emulsion polymerization, this means that the temperature is kept at a constant value from the start of the polymerization. Variations of +/−5° C., preferably +/−2° C. and especially +/−1° C. during the polymerization process are considered to be a constant temperature (based on the desired constant temperature value). The temperature is kept constant until the polymerization has ended, which is preferably the case after a conversion of more than 90% of the monomers used, more preferably more than 95% by weight and especially preferably at full conversion (100% by weight). The temperature can be kept constant by removing the heat of reaction which arises by cooling. The start of the polymerization is normally the addition of the polymerization initiator, preferably the addition of a redox initiator system. Normally, the system is first heated to the desired temperature and a constant temperature is awaited while stirring. Subsequently, the polymerization initiator is added, as a result of which the polymerization process commences. In one embodiment of the present invention, the temperature is kept constant at a value above the melting point of the associative monomer used.

In a preferred embodiment of the invention the polymerisation starts at low temperatures and is increasing during the polymerisation as described above until a special temperature is reached and then the polymerisation temperature is kept constant by cooling.

The present invention preferably provides surfactant-containing alkaline formulations comprising at least one inventive thickener according to the above definitions. The pH of the formulation is 7 to 13.

The inventive inverse dispersion containing acidic or alkaline surfactant-containing aqueous formulations may comprise further ingredients known to those skilled in the art. Suitable ingredients comprise one or more substances from the group of the builders, bleaches, bleach activators, enzymes, electrolytes, nonaqueous solvents, pH modifiers, fragrances, perfume carriers, fluorescers, dyes, hydrotropes, foam inhibitors, silicone oils, antiredeposition agents, optical brighteners, graying inhibitors, antishrink agents, anticrease agents, dye transfer inhibitors, active antimicrobial ingredients, germicides, fungicides, antioxidants, corrosion inhibitors, antistats, ironing aids, hydrophobizing and impregnating agents, swelling and antislip agents, UV absorbers and fabric softening compounds.

In one embodiment of the present invention, the surfactant-containing formulations, comprise less than 1% by weight of inverse dispersion (based on the overall formulation), the cationic polymer of the inverse dispersion being obtained by inverse emulsion polymerization at increasing temperature. Preferably, the formulations comprise 0.01 to <1% by weight of thickener.

The present invention further provides for the use of an inventive surfactant-containing acidic formulation in hair cosmetics, in hair styling, as a shampoo, as a softener, as a conditioner, as a skin cream, as a shower gel, as a fabric softener for laundry, or as an acidic detergent, preferably for toilets or baths.

The present invention further provides for the use of a surfactant-containing alkaline formulation as a liquid washing composition or as a machine or manual dishwashing detergent.

The present invention further provides for the use of the inventive thickener as a viscosity modifier, for optimization of shear dilution, as a thickening agent, for stabilization of suspended constituents having a size in the range from nanometers to millimeters and/or in surfactant-containing acidic or alkaline formulations.

The invention is illustrated hereinafter by the examples.

In the examples, the following abbreviations are used:

Monomers

ACM Acrylamide

DMA3*MeCl 2-trimethylammoniumethyl acrylate chloride or 2-(Acryloyloxy)ethyl]trimethylammonium chloride DMAEMA*MeCl 2-trimethylammoniumethyl methacrylate chloride BEM behenyl-25 methacrylate MBA methylene-bis-acrylamide (crosslinker)

TAAC tetraallyl-ammonium chloride (crosslinker)

NaHP sodium hypophosphite (chain transfer agent)

C16EO25MAc $C_{16}$-$C_{18}$-fatty alcohol-(ethylene glycol)$_{25}$ ether methacrylate Others pphm parts per hundred parts of monomers

EXAMPLES

General Test Methods

Unless stated otherwise, the following general test methods are used in the examples which follow:

Determination of Viscosity in Aqueous Media

With reference to the methods according to DIN 51550, DIN 53018, DIN 53019, the Brookfield model DV II viscometer is used, unless stated otherwise within the following tables, at the speed of 10 or 60 revolutions per minute with the specified spindle no. 2, 3 or 6 to measure the viscosities reported in mPas.

Determination of viscosity at 25° C. of 1 wt % aqueous solution product (approximately 50 wt % active polymer)—Brookfield viscosity is measured using a Brookfield DVII-fitted with a spindle 3 at 10 rpm. The test is conducted in deionised water at 25° C. Initial viscosity is defined as the Brookfield viscosity measured within 35 minutes of making the sample.

Determination of viscosity at 25° C. of an aqueous solution containing 0.4 wt % product (approximatively 50 wt % active polymer) and 100 ppm calcium chloride—Brookfield viscosity is measured using a Brookfield DVII—fitted with a spindle 2 at 60 rpm. The test is conducted in 100 ppm calcium chloride solution in deionised water at 25° C. Initial viscosity is defined as the Brookfield viscosity measured within 2 hours of making the sample.

Assessing Phase and Brookfield Viscosity Stability

Brookfield viscosity is measured using a Brookfield DV-E viscometer fitted with a LV2 spindle at 60 RPM. The test is conducted in accordance with the instrument's instructions. Initial viscosity is defined as the Brookfield viscosity measured within 24 hours of making the sample. Samples are stored in glass jars with a screw cap lid and aged undisturbed in a constant temperature room maintained at 35° C. Physical stability is assessed by visual observation of the product in the undisturbed glass jar. Products are deemed stable when no clear layer is observed at the bottom of the jar. Products are deemed unstable when a clear layer is observed at the bottom of the jar. Brookfield viscosity of the aged sample is measured after tipping the jar by hand to homogenize the sample.

Determining Viscosity Slope

Acidified water is prepared gravimetrically by adding about 0.1 ppm hydrochloric acid to deionized water. A series of aqueous polymer solutions are prepared to logarithmically span between 0.01 and 1 polymer weight percent of the polymer in said acidic water. Each polymer solvent solutions is prepared gravimetrically by mixing the polymer and solvent with a SpeedMixer DAC 150 FVZ-K (made by FlackTek Inc. of Landrum, S.C.) for 1 minute at 2,500 RPM in a Max 60 cup or Max 100 cup to the target polymer weight percent of the aqueous polymer solution. Viscosity as a function of shear rate of each polymer solvent solutions is measured at 40 different shear rates using an Anton Paar rheometer with a DSR 301 measuring head and concentric cylinder geometry. The time differential for each measurement is logarithmic over the range of 180 and 10 seconds and the shear rate range for the measurements is 0.001 to 500 1/s (measurements taken from the low shear rate to the high shear rate).

Viscosities 0.2 Pa s and greater at a shear rate of 0.01 1/s as a function of polymer weight percent of the aqueous polymer solvent solution was fit using the equation $Y=bX^a$ wherein X was the polymer concentration in the solvent polymer solution, Y was the polymer solvent solution viscosity, b was the extrapolated solvent polymer solution viscosity when X is extrapolated to one weight percent and the exponent a is the polymer concentration viscosity scaling power, here defined as the viscosity slope, over the polymer concentration range where the exponent a is the highest value. The range of viscosities fit with the equation and the resulting fit parameters are listed in Table T1.

Use of the Inventive Polymers in Standard Formulation of Fabric Softeners

W3: Preparation of a methyltris(hydroxyethyl)ammonium ditallow fatty acid ester methosulfate, partly hydrogenated, fabric softener (active content 5.5%)

The fabric softener has a pH of 2.7 and comprises 5.5% by weight of methyltris(hydroxyethyl)ammonium ditallow fatty acid ester methosulfate (partly hydrogenated) and 94.5% by weight of demineralized water.

Addition of 1 wt % Dispersion (Approximately 50 wt % Active Polymer) to Fabric Softener Formulations W3

The thickener is added gradually at room temperature to the particular fabric softener formulation and stirred until the formulation has homogenized.

The Brookfield viscosity is measured 2 h after the preparation using the Brookfield model DV II viscometer at the speed of 10 revolutions per minute with the specified spindle no. 6 reported in mPas. The results are compiled in Table 4.

Determination of the Soluble and Insoluble Parts of the Monomer Using the Analytical Ultracentrifuge (AUC)

For the determination of soluble and insoluble parts of the polymer, fractionation experiments using Analytical ultracentrifugation were performed. Sedimentation velocity runs using a Beckman Optima XL-I (Beckman Instruments, Palo Alto, USA) with interference optical detection system (wavelength 675 nm) was used. The samples have been measured at polymer concentrations below critical polymer overlap concentration using salt solution to insure polyelectrolyte screening effect. The centrifugation speed was varied between 1000 rpm and 45,000 rpm.

The—sedimentation coefficient—, defined as—a median value for each fraction, and the concentration of one sedimenting fraction were determined using a standard analysis Software (SED-FIT) using the density and viscosity of the solvent, and a specific refractive index increment of the polymer. The sedimentation coefficient is in units of Sved (1 Sved=$10^{-13}$ seconds). The standard deviation for the determination of weight fraction and sedimentation coefficients of water soluble and crosslinked water-swellable polymers is 3%, 10% and up to 30% respectively Fabric and Test Swatch Preparation Method Fabrics are assessed under NA Top Load wash conditions using Kenmore FS 600 and/or 80 series washer machines. Wash Machines are set at: 90° F./60° F. wash/rinse temperature, 6 gpg hardness, normal cycle, and medium load (17 gallon). Fabric bundles consist of 5.5 pounds of clean fabric consisting of 100% cotton. Test swatches are included with this bundle and comprise of 100% cotton Euro Touch terrycloth towels (purchased from Standard Textile, Inc. Cincinnati, Ohio). Bundles are stripped according to the Fabric Preparation-Stripping and Desizing procedure before running the test. Tide Free liquid detergent (1× recommended dose) is added under the surface of the water after the machine is at least half full. Once the water stops flowing and the washer begins to agitate, the clean fabric bundle is added. When the machine is almost full with rinse water, and before agitation has begun, the fabric care testing composition is slowly added (1× dose), ensuring that none of the fabric care testing composition comes in direct contact with the test swatches or fabric bundle. When the wash/rinse cycle is complete, each wet fabric bundle is transferred to a corresponding dryer. The dryer used is a Maytag commercial series (or equivalent) dryer, with the timer set for 55 minutes on the cotton/high heat/timed dry setting. Once the dryer stops, 12 Terry towels from each fabric bundle are removed for actives deposition analysis. The fabrics are then placed in a constant Temperature/Relative Humidity (70° F., 50% relative humidity) controlled grading room for 12-24 hours and then graded for softness and/or actives deposition.

The Fabric Preparation-Stripping and Desizing procedure includes washing the clean fabric bundle (5.5 lbs of fabric comprising 100% cotton) including the test swatches of 100% cotton EuroTouch terrycloth towels for 5 consecutive wash cycles followed by a drying cycle. AATCC (American Association of Textile Chemists and Colorists) High Efficiency (HE) liquid detergent is used to strip/de-size the test swatch fabrics and clean fabric bundle (1× recommended dose per wash cycle). The wash conditions are as follows: Kenmore FS 600 and/or 80 series wash machines (or equivalent), set at: 120° F./120° F. wash/rinse temperature, water hardness equal to 0 gpg, normal wash cycle, and medium sized load (17 gallon). The dryer timer is set for 55 minutes on the cotton/high/timed dry setting.

Silicone Measurement Method

Silicone is extracted from approximately 0.5 grams of fabric (previously treated according to the test swatch treatment procedure) with 12 mL of either 50:50 toluene:methylisobutyl ketone or 15:85 ethanol:methylisobutyl ketone in 20 mL scintillation vials. The vials are agitated on a pulsed vortexer for 30 minutes. The silicone in the extract is quantified using inductively coupled plasma optical emission spectrometry (ICP-OES). ICP calibration standards of known silicone concentration are made using the same or a structurally comparable type of silicone raw material as the products being tested. The working range of the method is 8-2300 µg silicone per gram of fabric. Concentrations greater than 2300 µg silicone per gram of fabric can be assessed by subsequent dilution. Deposition efficiency index of silicone is determined by calculating as a percentage, how much silicone is recovered, via the aforementioned measurement technique, versus how much is delivered via the formulation examples. The analysis is performed on terrycloth towels (EuroSoft towel, sourced from Standard Textile, Inc, Cincinnati, Ohio) that have been treated according to the wash procedure outlined herein.

Stabilizing Agents Used in the Examples

Stabilizing agent A (nonionic block copolymer): PEG-75-dipoly-ω-hydroxystearate.

Stabilizing agent B is a nonionic ABA-block copolymer with molecular weight of about 5000 g/mol, and a hydrophobic lipophilic balance value (HLB) of 5 to 6, wherein the A block is based on polyhydroxystearic acid and the B block on polyalkylene oxide oxide which comprises about 15 ethylene oxide units.

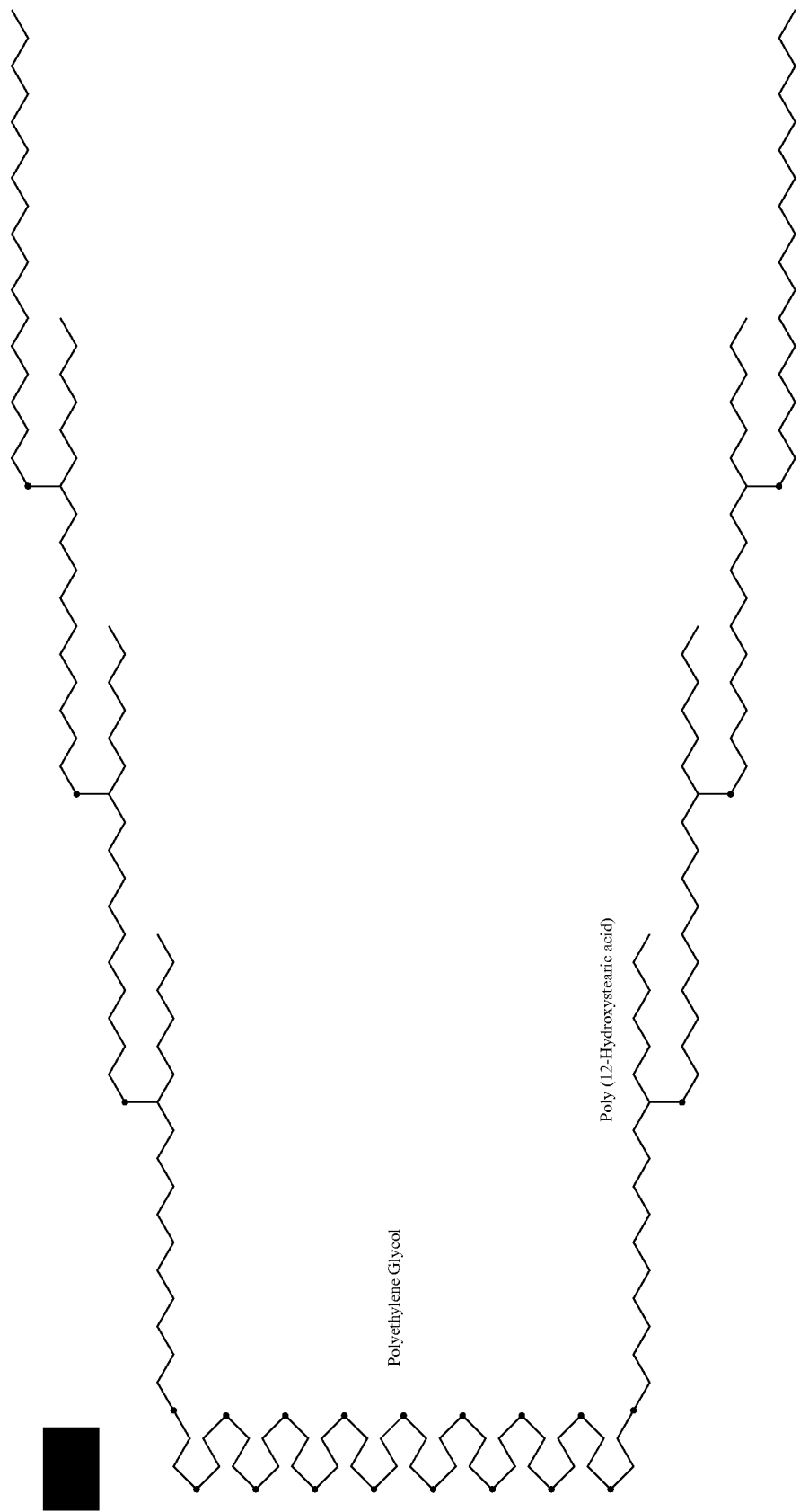

Stabilizing agent C (nonionic block copolymer): PEG-30 Dipoly(12-hydroxystearic acid)
Stabilizing agent D (nonionic block copolymer): Alcyd Polyethylenglycol Poly-isobutene stabilizing surfactant with HLB 5-7
  Oil soluble group: poly-iso-butylene
  Anchoring group: polyethylene glycol
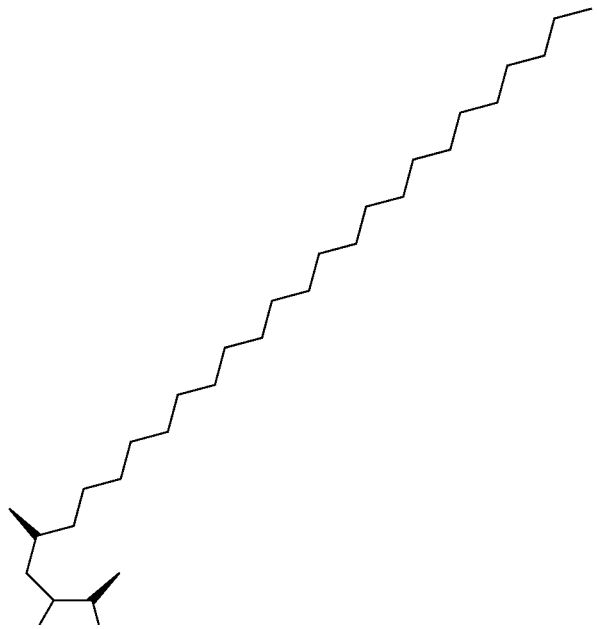
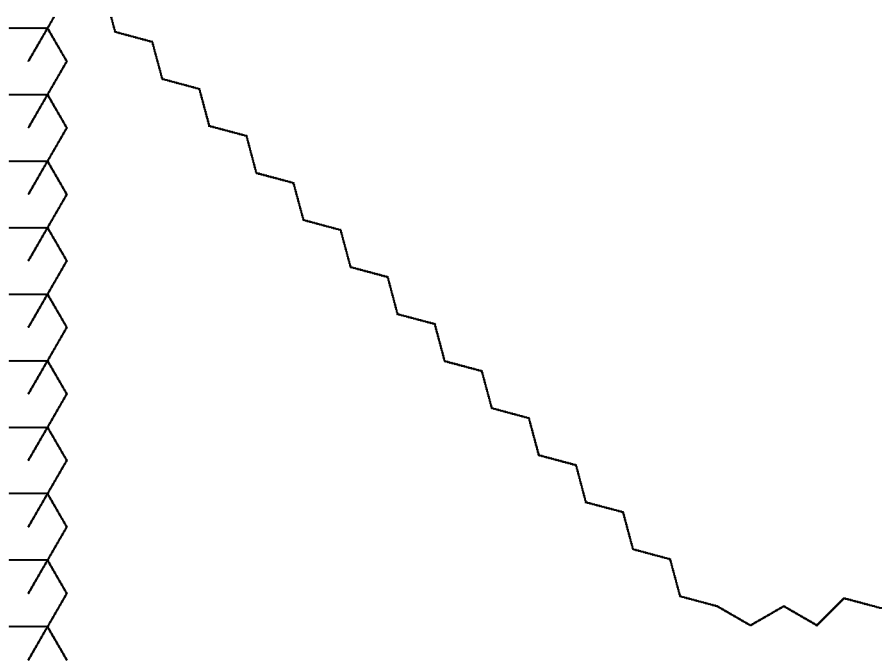

-continued

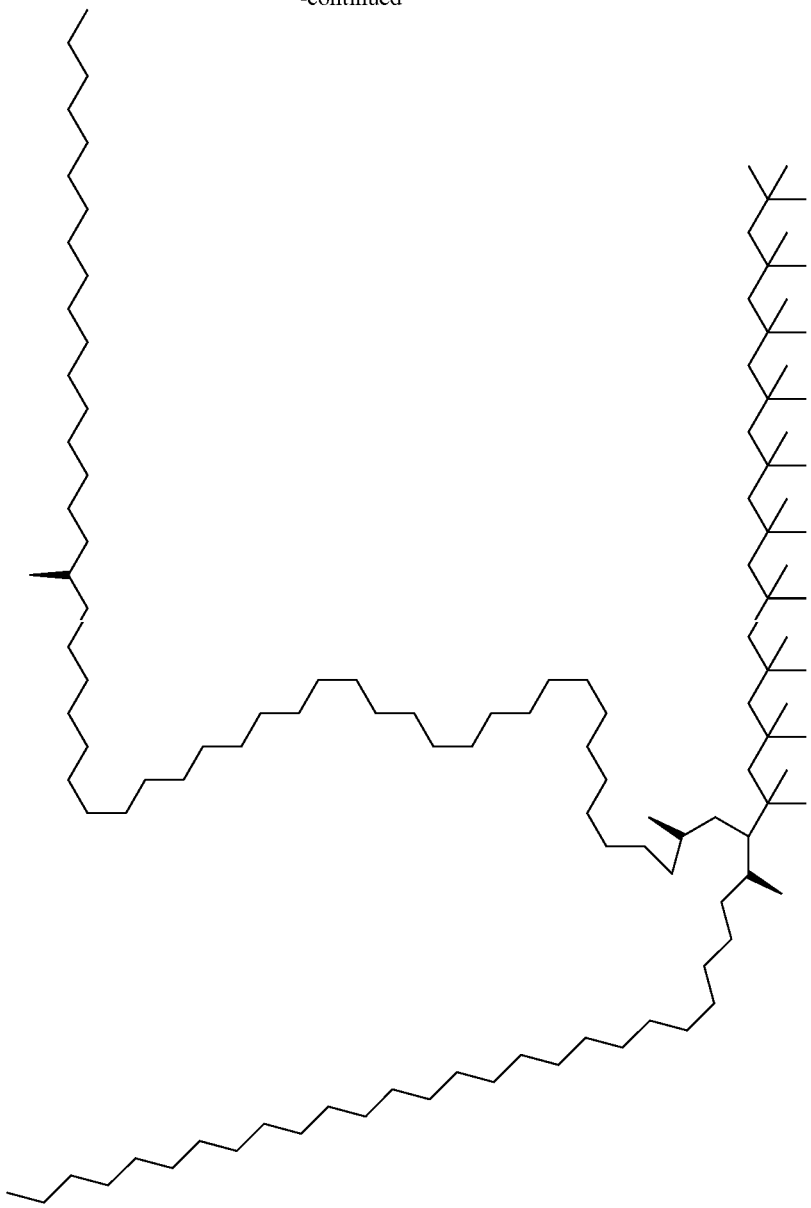

Comparative Example 1 (CE1)

Synthesis of the Cationic Polymer

An aqueous phase of water soluble components is prepared by admixing together the following components:
1.23 g (0.5 pphm) of citric acid-1-hydrate,
0.7 g (0.29 pphm) of a aqueous solution of pentasodium diethylenetriaminepentaacetate,
43.78 g (17.85 pphm) of water,
29.56 g (0.12 pphm) of methylene-bis-acrylamide (1% aqueous solution),
8.0 g (0.02 pphm) tetraallylammonium chloride (TAAC) (5% aqueous solution),
8.0 g (0.02 pphm) of sodium hypophosphite (5% aqueous solution), and
326.66 g (100.0 pphm) of methyl chloride quaternised dimethylaminoethylmethacrylate.

An oil phase is prepared by admixing together the following components:

8.0 g (2.45 pphm) of sorbitan tri-oleate (75% in dearomatized aliphatic hydrocarbon) point between 160° C. till 190° C.
67.8 g (5.22 pphm) of a polymeric stabilizer (stearyl methacrylate-methacrylic acid copolymer: (18.87% in solvent)
151.29 g (61.75 pphm) of 2-ethylhexyl stearate, and
60.2 g (24.57 pphm) of dearomatised hydrocarbon solvent with a boiling point between 160° C. till 190° C.

The two phases are mixed together in a ratio of 41.8 parts oil phase to 58.2 parts aqueous phase under high shear to form a water-in-oil emulsion. The resulting water-in-oil emulsion is transferred to a reactor equipped with nitrogen sparge tube, stirrer and thermometer. The emulsion is purged with nitrogen to remove oxygen.

Polymerisation is effected by addition of a redox couple of sodium metabisulphite and tertiary butyl hydroperoxide stepwise such that is a temperature increase of 2° C./min.

Once the isotherm has been attained, a free radical initiator (2,2'-azobis(2-methylbutyronitrile), CAS: 13472-08-7) is added in two steps (the 2nd step after 45 min) and the emulsion is kept at 85° C. for 75 minutes.

Vacuum distillation is carried out to remove water and volatile solvent to give a final product of 50% polymer solids.

To this product addition is made of 34.3 g (14.0 pphm) of a fatty alcohol alkoxylate [alcohol C6-C17(secondary) poly(3-6)ethoxylate: 97% secondary alcohol ethoxylate+3% poly(ethylene oxide)], (CAS No. 84133-50-6).

Comparative Example 2 (CE2)

Synthesis of the Cationic Polymer

This example illustrates the preparation of a suitable cationic polymer.

An aqueous phase of water soluble components is prepared by admixing together the following components:
1.88 g (0.5 pphm) of citric acid-1-hydrate,
1.07 g 0.29 pphm) of a aqueous solution of pentasodium diethylenetriaminepentaacetate,
220.37 g (58.77 pphm) of water,
3.75 g (0.01 pphm) of methylene-bis-acrylamide (1% aqueous solution),
0.75 g (0.2 pphm) of formic acid
281.25 g (60.0 pphm) of methyl chloride quaternised dimethylaminoethylacrylate (DMA3*MeCl 80% aqueous solution), and
300.00 g (40.0 pphm) of acrylamide (50% aqueous solution).

An oil phase is prepared by admixing together the following components:
12.245 g (2.45 pphm) of sorbitan tri-oleate (75% in dearomatized aliphatic hydrocarbon) point between 160° C. till 190° C.
103.825 g (5.22 pphm) of a polymeric stabiliser, stearyl methacrylate-methacrylic acid copolymer (18.87% in solvent)
259.14 g (69.1 pphm) of 2-ethylhexyl stearate, and
99.97 g (26.66 pphm) of dearomatised hydrocarbon solvent with a boiling point between 160° C. till 190° C.

The two phases are mixed together in a ratio of 37 parts oil phase to 63 parts aqueous phase under high shear to form a water-in-oil emulsion. The resulting water-in-oil emulsion is transferred to a reactor equipped with nitrogen sparge tube, stirrer and thermometer. 0.21 g (0.056 pphm) Wako V59 is added and the emulsion is purged with nitrogen to remove oxygen.

Polymerisation is effected by addition of a redox couple of sodium metabisulphite and tertiary butyl hydroperoxide stepwise such that is a temperature increase of 2° C./min. After the isotherm is completed the emulsion held at 85° C. for 60 minutes. Then residual monomer reduction with 72.7 g (0.25 pphm) tertiary butyl hydroperoxide (1.29% in solvent) and 82.2 g (0.25 pphm) sodium metabisulphite (1.14% in emulsion) is started (3 hours feeding time).

Vacuum distillation is carried out to remove water and volatile solvent to give a final product, i.e. a dispersion containing 50% polymer solids.

To this product addition is made of 52.5 g (14.0 pphm) of Tergitol 15-S-7 (secondary alcohol ethoxylated).

Example 2 with enhanced soluble polymer part and improved deposition and enhanced stability Synthesis of the Cationic Polymer This example illustrates the preparation of a suitable cationic polymer.

An aqueous phase of water soluble components is prepared by admixing together the following components:
1.88 g (0.5 pphm) of citric acid-1-hydrate,
1.07 g (0.29 pphm) of a aqueous solution of pentasodium diethylenetriaminepentaacetate,
220.37 g (58.77 pphm) of water,
3.75 g (0.01 pphmof methylene-bis-acrylamide (1% aqueous solution),
0.75 g (0.2 pphm) of formic acid
281.25 g (60.0 pphm) of methyl chloride quaternised dimethylaminoethylacrylate (DMA3*MeCl80% aqueous solution), and
300.00 g (40.0 pphm) of acrylamide (50% aqueous solution).

An oil phase is prepared by admixing together the following components:
45.92 g (2.45 pphm) of stabilizing agent B (20% in solvent) as stabilizing surfactant,
103.825 g (5.22 pphm) of a polymeric stabiliser stearyl methacrylate-methacrylic acid copolymer (18.87% in solvent),
295.13 g (78.7 pphm) of 2-ethylhexyl stearate, and
30.3 g (8.08 pphm) of dearomatised hydrocarbon solvent with a boiling point between 160° C. till 190° C.

The two phases are mixed together in a ratio of 37 parts oil phase to 63 parts aqueous phase under high shear to form a water-in-oil emulsion. The resulting water-in-oil emulsion is transferred to a reactor equipped with nitrogen sparge tube, stirrer and thermometer. 0.38 g (0.1 pphm) Wako V59 is added and the emulsion is purged with nitrogen to remove oxygen.

Polymerisation is effected by addition of a redox couple of sodium metabisulphite and tertiary butyl hydroperoxide stepwise such that is a temperature increase of 2° C./min. After the isotherm is completed the emulsion held at 85° C. for 60 minutes. Then residual monomer reduction with 72.7 g (0.25 pphm) tertiary butyl hydroperoxide (1.29% in solvent) and 82.2 g (0.25 pphm) sodium metabisulphite (1.14% in emulsion) is started (3 hours feeding time).

Vacuum distillation is carried out to remove water and volatile solvent to give a final product, i.e. a dispersion containing 50% polymer solids.

To this product addition is made of 52.5 g (14.0 pphm) of a fatty alcohol alkoxylate [alcohol C6-C17(secondary) poly(3-6)ethoxylate: 97% secondary alcohol ethoxylate+3% poly(ethylene oxide)], (CAS No. 84133-50-6).

Examples 2. 1 to 2.6 are prepared according to the same process as the one described above for example 2. Concerning example 2.5. the oxidizing redox initiator component t-butylhydroperoxide was replaced in the first half of the polymerization process by potassium bromate and was fed to the aqueous phase

TABLE 1

Examples 2.1 till 2.6

| example | Sorbitan Trioleate (pphm) | Stabilizing agent B (pphm) | DMAEMA*MeCl (pphm) | DMA3*MeCl (pphm) | Acrylamide (pphm) | Methylen bis acrylamide (pphm) | Reaction-speed ° C./min. |
|---|---|---|---|---|---|---|---|
| CE1 | 2.45 | | 100. | | | 0.12 | +2 |
| CE2 | 2.45 | | | 60 | 40 | 0.01 | +2 |
| Example 2 | | 2.45 | | 60 | 40 | 0.01 | +2 |
| Example 2.1 | | 2.45 | | 50 | 50 | 0.075 | +1 |
| Example 2.2 | | 2.45 | | 70 | 30 | 0.01 | +1 |
| Example 2.3 | | 2.45 | | 80 | 20 | 0.01 | +1 |
| Example 2.4 | | 2.45 | | 90 | 10 | 0.01 | +1 |
| Example 2.5 | | 2.45 | | 60 | 40 | 0.01 | +2 |
| Example 2.6 | | 2.45 | | 50 | 50 | 0 | +1 |

Example 2.1-2.4: a ratio of 43 parts oil phase to 57 parts aqueous phase!

Examples with stabilizing agents A, C and D lead to comparable results as those obtained when using stabilizing agent B.

TABLE 2

Viscosities and viscosity slope of examples 2.1 till 2.6 and CE1 and 2

| example | Viscosity (mPa * s) of 1% product in deionized water measured at 30 min (RT) | Viscosity (mPa * s) of aqueous solution containing 0.4% product and 100 ppm calcium chloride solution measured at 2 h (RT) | Viscosity (mPa * s) of formulation W3 containing 1 wt % product-measured at 2 h (RT) | Viscosity slope |
|---|---|---|---|---|
| CE1 | 24 000 | 113 | 6300 | 5.9 |
| CE2 | 14300 | 209 | 8300 | 5.1 |
| Example 2 | 7200 | 424 | 6400 | 4.9 |
| Example 2.1 | 7880 | 289 | 6100 | 4.9 |
| Example 2.2 | 6480 | 415 | 6000 | 4.4 |
| Example 2.3 | 5870 | 398 | 5900 | 3.9 |
| Example 2.4 | 2040 | 216 | 4000 | 1.9 |
| Example 2.5 | 120 | 480 | 1100 | not available |
| Example 2.6 | 7980 | 28 | 6400 | 0.51 |

TABLE 3

Storage Stability

| Example | After 3 weeks at 25° C. | After 4 months at 25° C. | After 6 months at 25° C. |
|---|---|---|---|
| CE 1 | Visible fine dispersed coagulum | serum, sediment, redispersable | serum, sediment, redispersable |
| CE 2 | Visible fine dispersed coagulum | serum, sediment, redispersable | serum, sediment, redispersable |
| Example 2 | stable | stable | stable |
| Example 2.1 | stable | stable | stable |
| Example 2.2 | stable | stable | stable |
| Example 2.3 | stable | stable | stable |
| Example 2.4 | stable | stable | stable |
| Example 2.5 | stable | stable | stable |
| Example 2.6 | stable | stable | stable |

If after storage time there is no solvent on top of the dispersion without polymer particles, called serum, and no polymer particles sedimented down after storage at room temperature and no coagulum formed by aggregation of 2 or more particles the inverse polymer dispersion is called stable.

TABLE 4

Sedimentation Coefficient of examples 2.1 till 2.6. and comparative examples CE1 and 2:

| Example | Sedimentation Coefficient For soluble part | Sedimentation Coefficient For insoluble part | Wt % for soluble part | Wt % for insoluble part |
|---|---|---|---|---|
| CE 1 | 5.7 | 25000 | 9 | 91 |
| CE 2 | 7 | 8400 | 20 | 80 |
| Example 2 | 6 | 6050 | 31 | 69 |
| Example 2.1 | 6 | 7400 | 25 | 75 |
| Example 2.2 | 5 | 8650 | 30 | 70 |
| Example 2.3 | 6 | 6500 | 31 | 69 |
| Example 2.4 | 7 | 2600 | 58 | 42 |
| Example 2.5 | 6 | 6050 | 32 | 68 |
| Example 2.6 | 4 | none | 100 | 0 |

TABLE 5 finished product deposition performance in example Formula II using dispersions from Table 8

| Dispersion in Formula II Chassis | Polymer Level (wt. %) | Initial Brookfield Viscosity (cPs) | After 12 wks @ 35° C. Brookfield Viscosity (cPs) | Physical Stability |
|---|---|---|---|---|
| P1 | 0.2 | 132 | 233 | 5% split |
| P3 | 0.2 | 379 | 494 | stable, but high visc. |
| P4 | 0.2 | 28 | 39 | stable |

TABLE 6 finished product deposition performance in example Formula IV using Linear Cationic methacrylate acrylamide copolymer (dispersion from Table 1 Example 2.6)

| Polymer Level (wt. %) | Initial Brookfield Viscosity (cPs) | After 12 wks @ 35° C. Brookfield Viscosity (cPs) | Physical Stability | Silicone (ug/g Fabric) |
|---|---|---|---|---|
| 0.015 | 43 | 191 | stable | 99 |
| 0.0 | 45 | 192 | stable | 31 |

TABLE 7

Example Formulas
The following are non-limiting examples of the fabric care compositions -

| (% wt) | FI | FII | FIII | FIV | FV |
|---|---|---|---|---|---|
| FSA[a] | 11 | 11 | 7 | 11 | 17 |
| Low MW Alcohol[b] | 1.00 | 1.00 | 0.6 | 1.00 | 0.7 |
| Structurant[c] | — | — | — | 0.075 | — |
| Perfume | 1.75 | 1.75 | 0.56 | 1.75 | 1.75 |
| Perfume encapsulate[d] | 0.69 | 0.69 | 0.26 | 0.69 | 0.69 |
| Calcium Chloride (ppm) | 547 | 547 | 200 | 547 | 750 |
| Chelant[e] | 0.007 | 0.007 | 0.036 | 0.007 | 0.007 |
| Preservative (ppm)[f] | 5 | 5 | 5 | 5 | 5 |
| Acidulent (ppm) (Formic Acid) | 260 | 260 | 260 | 260 | 260 |
| Antifoam[g] | 0.015 | 0.015 | 0.008 | 0.015 | 0.015 |
| Cationic methacrylate acrylamide copolymer[h] | 0.20 | 0.20 | 0.30 | — | 0.15 |
| Linear Cationic methacrylate acrylamide copolymer[i] | — | — | — | 0.015 | — |
| Water soluble dialkyl quat[j,k] | 0.25 | — | — | — | — |
| Dispersant[l] | — | 1.00 | 0.67 | 1.00 | — |
| Stabilizing Surfactant[m] | — | — | — | — | 0.25 |
| PDMS emulsion[n] | — | — | — | — | 0.65 |
| Amino-functional Organosiloxane Polymer[o] | 3.00 | 3.00 | 2.00 | 3.00 | — |
| Dye (ppm) | 30 | 30 | 20 | 30 | 30 |
| Hydrochloric Acid | 0.025 | 0.025 | 0.014 | 0.025 | 0.020 |
| Deionized Water | Balance | Balance | Balance | Balance | Balance |

[a]N,N-di(tallowoyloxyethyl)-N,N-dimethylammonium chloride.
[b]Low molecualr alcohol such as EtOH or IPA
[c]Cationic polymer available from BASF under the tradename Rheovis ® CDE.
[d]Perfume microcapsules available ex Appleton Papers, Inc.
[e]Diethylenetriaminepentaacetic acid or hydroxyl ethylidene-1,1-diphosphonic acid
[f]1,2-Benzisothiazolin-3-ONE (BIT) under the trade name Proxel available from Lonza
[g]Silicone antifoam agent available from Dow Corning ® under the trade name DC2310.
[h]Cationic acrylates-acrylamide copolymers P1-P5 from Table 8.
[i]Linear co-polymer of DMA3*MeCl and Acrylamide at a ratio 60:40, DMA3*MeCl:Acrylamide (dispersion from Table 1 Example 2.6)
[j]Didecyl dimethyl ammonium chloride under the trade name Bardac ® 2280
[k]Hydrogenated tallowalkyl(2-ethylhexyl)dimethyl ammonium methylsulfate from AkzoNobel under the trade name Arquad ® HTL8-MS
[l]Non-ionic surfactant from BASF under the trade name Lutensol ® XL-70
[m]Non-ionic surfactant, such as TWEEN 20 ™ or TAE80 (tallow ethoxylated alcohol, with average degree of ethoxylation of 80), or cationic surfactant as Berol 648 and Ethoqua ® C 25 from Akzo Nobel
[n]Polydimethylsiloxane emulsion from Dow Corning under the trade name DC346 ®.
[o]Amino-functional Organosiloxane polymer such as aminoethylaminopropylmethylsiloxane-dimethylsiloxane copolymer with an amine equivalent of 1500 g/mol or greater (commercially available from Shin-Etsu Silicones under the name KF-861, KF-8002)

TABLE 8

Example P1 till P5

| example | Sorbitan Trioleate (pphm) | Stabilizing surfactant B (pphm) | DMAEMA* MeCl (pphm) | DMA3* MeCl (pphm) | Acrylamide (pphm) | Methylen bis acryla-acrylamide (pphm) | Reaction-speed ° C./min. | Process |
|---|---|---|---|---|---|---|---|---|
| P1 | 2.45 | | | 60 | 40 | 0 | +2 | CE 2 without crosslinker |
| P3 | 2.45 | | | 60 | 40 | 0.005 | +2 | CE 2 with half amount of crosslinker |
| P4 | | 2.5 | | 50 | 50 | 0.01 | +1 | CE 1 with low amount of crosslinker |

The invention claimed is:
1. An inverse dispersion comprising
i) at least one cationic polymer obtainable by the polymerization of
a) at least one cationic monomer and optionally at least one nonionic monomer (compound A),
b) at least one crosslinker (compound B), wherein the amount of crosslinker lies in the range of from 0 to 0.01% by weight based on the total amount of compounds A to C,
c) at least one chain transfer agent (compound C),
ii) at least one stabilizing agent, wherein the stabilizing agent has one or more hydrophobic units with more than 30 carbon atoms per hydrophobic unit, and wherein the stabilizing agent has a hydrophilic-lipophilic balance value of from 1 to 9,
iii) at least an oil phase,
wherein the ratio of the stabilizing agent to the cationic polymer is from 0.1 wt % to 20 wt %.
2. The inverse dispersion according to claim 1, wherein the stabilizing agent has one or more hydrophobic units with more than 50 carbon atoms per hydrophobic unit.
3. The inverse dispersion according to claim 1, wherein compound A comprises at least one cationic monomer and at least one nonionic monomer.
4. The inverse dispersion according to claim 1, wherein the weight ratio of cationic monomer to nonionic monomer lies in the range of from 90:10 to 10:90.
5. The inverse dispersion according to claim 1, wherein the cationic monomer is selected from a compound of the formula (I)

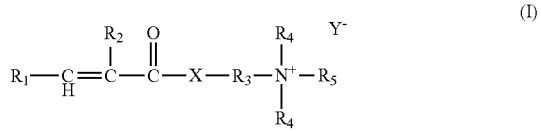

where
$R_1$ is H or $C_1$-$C_4$-alkyl,
$R_2$ is H or methyl,
$R_3$ is $C_1$-$C_4$-alkylene,
$R_4$, $R_5$ and $R_6$ are each independently H or $C_1$-$C_{30}$-alkyl,
X is —O— or —NH—, and
Y is Cl, Br, I, hydrogensulfate or methosulfate.
6. The inverse dispersion according to claim 1, wherein the cationic monomer is 2-(Acryloyloxy)ethyl]trimethylammonium chloride.
7. The inverse dispersion according to claim 1, wherein the nonionic monomer is selected from N-vinylpyrrolidone, N-vinylimidazole or a compound according to the formula (II)

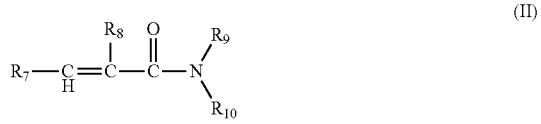

where
$R_7$ is H or $C_1$-$C_4$-alkyl,
$R_8$ is H or methyl, and
$R_9$ and $R_{10}$, independently of one another, are H or $C_1$-$C_{30}$-alkl, 8. The inverse dispersion according to claim 1, wherein the nonionic monomer is acrylamide.
9. The inverse dispersion according to claim 1, wherein compound B is required and is divinylbenzene, tetraallylammonium chloride, an allyl acrylate, an allyl methacrylate, a diacrylate or dimethacrylate of glycol or polyglycol, butadiene, 1,7-octadiene, an allylacrylamide or allylmethacrylamide, a bisacrylamidoacetic acid, N,N'-methylenebisacrylamide or a polyol polyallyl ether.
10. The inverse dispersion according to claim 1, wherein compound C is required and is a mercaptan, lactic acid, formic acid, isopropanol or a hypophosphite.
11. The inverse dispersion according to claim 1, wherein the stabilizing agent has a hydrophilic-lipophilic balance value of from 3 to 9.
12. The inverse dispersion according to claim 1, wherein the stabilizing agent has a hydrophilic-lipophilic balance value of from 5 to 7.
13. The inverse dispersion according to claim 1, wherein the stabilizing agent has a block-structure, graft-structure or comb-structure.
14. The inverse dispersion according to claim 1, wherein the stabilizing agent has an ABA block-structure based on polyhydroxystearic acid as an A block and polyalkylene oxide as a B block.
15. The inverse dispersion according to claim 1, wherein from 10% to 100% by weight based on the total weight of the cationic polymer are water-soluble polymers.
16. The inverse dispersion according to claim 15, wherein the water- soluble polymers of the cationic polymer have a sedimentation coefficient of from 0.1 to 100Sved in aqueous media.
17. The inverse dispersion according to claim 1, wherein crosslinked water-swellable polymers are present in an amount up to 90% by weight based on the total weight of the cationic polymer.
18. The inverse dispersion according to claim 17, wherein the crosslinked water-swellable polymers have a sedimentation coefficient of more than 300Sved in aqueous media.
19. The inverse dispersion according to claim 1, wherein the inverse dispersion displays a viscosity slope in aqueous media of from about 3.7 to about 6.5.
20. A process for the manufacture of an inverse dispersion comprising mixing
i) at least one cationic polymer obtainable by polymerizing
a) at least one cationic monomer and optionally at least one nonionic monomer,
b) at least one crosslinker, wherein the amount of crosslinker lies in the range of from 0 to 0.01% by weight based on the total amount of compounds A to C,
c) at least one chain transfer agent,
ii) at least one stabilizing agent, wherein the stabilizing agent has one or more hydrophobic chains with more than 30 carbon atoms, and wherein the stabilizing agent has a hydrophilic-lipophilic balance value of 1 to 9,
iii) at least one oil phase,
wherein the inverse dispersion is obtained by inverse emulsion polymerization, optionally followed by distillation by means of the liquid dispersion polymer technology,
wherein the ratio of the stabilizing agent to the cationic polymer is from 0.1 wt % to 20 wt %.
21. The process of claim 20, wherein the stabilizing agent has one or more hydrophobic chains with more than 50 carbon atoms.

* * * * *